United States Patent [19]

Chang

[11] Patent Number: 4,991,742
[45] Date of Patent: Feb. 12, 1991

[54] AUTOMATIC DRIP BOTTLE SET

[76] Inventor: Chin-Fu Chang, No. 166-1, Chang Nan Road, Changhua, Taiwan

[21] Appl. No.: 387,808

[22] Filed: Aug. 1, 1989

[51] Int. Cl.⁵ ............................................. B65D 35/28
[52] U.S. Cl. ...................................... 222/95; 222/105; 222/181; 222/156; 222/336; 222/386.5; 604/135
[58] Field of Search .................... 222/92, 95, 105, 107, 222/181, 185, 325, 215, 327, 336, 340, 386, 386.5, 156; 604/131–135

[56] References Cited

U.S. PATENT DOCUMENTS

| 103,640 | 5/1870 | Merritt | 222/103 X |
| 720,902 | 2/1903 | Brau | 222/95 |
| 1,880,354 | 10/1932 | Mueller | 222/95 X |
| 3,847,304 | 11/1974 | Cohen | 222/387 X |
| 3,871,554 | 3/1975 | Huck | 222/340 X |
| 3,902,635 | 9/1975 | Jinotti | 222/340 X |
| 4,077,544 | 3/1978 | Malacheski et al. | 222/95 |
| 4,160,513 | 7/1979 | Cockerham | 222/181 |
| 4,193,513 | 3/1980 | Bull, Jr. | 222/95 X |

Primary Examiner—Michael S. Huppert
Assistant Examiner—Kenneth DeRosa
Attorney, Agent, or Firm—Bacon & Thomas

[57] ABSTRACT

An automatic drip bottle set for medical drip infusion which includes an expansion drip bottle received in a cylinder covered by a spring pressure assembly having a hanger mounted thereon at the top for suspending the set, and a spring received therein to provide a pressure force against the expansion drip bottle to permit the infusion solution contained therein to be smoothly infused into the patient's body.

2 Claims, 2 Drawing Sheets

AUTOMATIC DRIP BOTTLE SET

BACKGROUND OF THE INVENTION

1. Field of the Invention

The present invention is related to a further improvement made on the automatic drip bottle set for medical drip infusion as disclosed in U.S. patent application Ser. No. 276,485 which has been abandoned, and more particularly to a drip bottle set which includes a hollow cylinder connected with a spring pressure assembly to provide a constant pressure force on an expansion drip bottle which is set therein, so as to let the infusion solution of the expansion drip bottle be smoothly infused into the blood circulation of a patient's body.

2. Description of the Prior Art

Through collective endeavors of people, the rapid development of advanced technology helps to improve the standard of living from physical and mental standpoints. However, following the development of the modern society, various problems arise to deteriorate the quality of the environment of the world and to further threaten human life. These problems may include air pollution, water pollution, environment pollution, traffic jam, etc., and the problems have become increasingly more serious each day. In order to maintain enjoying a happy life, people have now become more health conscious. Therefore, exercises and activities pertaining to health care have now become more attractive to people, and hospitals and clinical centers are being established everywhere in cities as well as in the countryside. Consequently, the demand for health care and medical equipment is increasing.

In medical treatment, drip infusion is quite commonly applied. For drip infusion, a drip bottle must be used to contain the infusion solution and permit the infusion solution to be dripped into the patient's body. A conventional drip infusion set normally includes a glass drip bottle for containing the infusion solution, which bottle is wrapped with a netted plastic wrapper for suspension from a drip infusion stand and connected with a tubing assembly which includes a drop-adapter, regulating clamp, glass observing adapter and injection needle. By means of a pressure difference, the infusion solution is drip infused into the body of the patient through the patient's blood circulation.

According to the conventional pressure difference method of permitting infusion solution to be drip infused into the patient's body through patient's blood circulation, when the solution contained in the drip bottle is reduced the air pressure inside the bottle is simultaneously reduced, and, in consequence, the infusion speed is caused to slow down. Therefore, the nurse who is normally in charge of caring for several patients at a time will become very busy in observing the infusion flow rates and adjusting the regulating clamps in order to maintain a smooth drip infusion speed for each bottle. This is very burdensome to the nurse who is usually busy with other duties.

Further, the refuse treatment of the waste drip bottles and the related wrappers and accessories is still another problem to handle. Because conventional drip bottles are made of glass, they require large receiving spaces for collection. Therefore, the cost of disposing waste drip infusion sets is quite expensive.

According to U.S. Pat. Nos. 720,902 and 3,847,304, known to use of a spring means for applying a pressure force onto the liquid solution to facilitate the discharging. However, due to the separate arrangement of the spring, pressure plate and cover, these known structures are not convenient for application in drip infusion.

SUMMARY OF THE INVENTION

The present invention provides an improved spring means for applying a pressure force on an infusion solution so as to let the infusion solution to be smoothly drip-infused through a tubing into the patient's body.

The main object of the present invention is to provide an automatic drip bottle set for medical drip infusion which includes a spring pressure assembly to provide a constant pressure force to press on an expansion drip bottle set in a hollow cylinder so as to let the infusion solution contained in the expansion drip bottle to be smoothly infused into the patient at a constant speed to follow the blood circulation of the patient.

Another object of the present invention is to provide an automatic drip bottle set for medical drip infusion which includes a hollow cylinder provided with inspection windows at a lower position thereof through which the amount of the infusion solution contained is clearly visible, and having two opposed "J" shaped notches for connection thereto by two opposed dowels of a spring pressure assembly.

A further object of the present invention is to provide an automatic drip bottle set for medical drip infusion wherein a spring pressure assembly is received in a hollow cylinder and firmly connected thereto by engaging two opposed dowels of a spring pressure assembly in two opposed "J" shaped notches of a hollow cylinder and turning the two dowels into inner corners of the "J" shaped notches.

A yet further object of the present invention is to provide an automatic drip bottle set for medical drip infusion which is detachably comprised of a hollow cylinder connected with a spring pressure assembly for replaceably setting therein of an expansion drip bottle, wherein the hollow cylinder and the spring pressure assembly are durable and reusable, and the expansion drip bottle is disposable and may be reduced in size to facilitate refuse treatment.

BRIEF DESCRIPTION OF THE DRAWINGS

The foregoing and other objects, features and advantage of the present invention will be best understood from the following detailed description, when considered in conjunction with the accompanying drawings in which.

DETAILED DESCRIPTION OF THE INVENTION

Figure 1A:
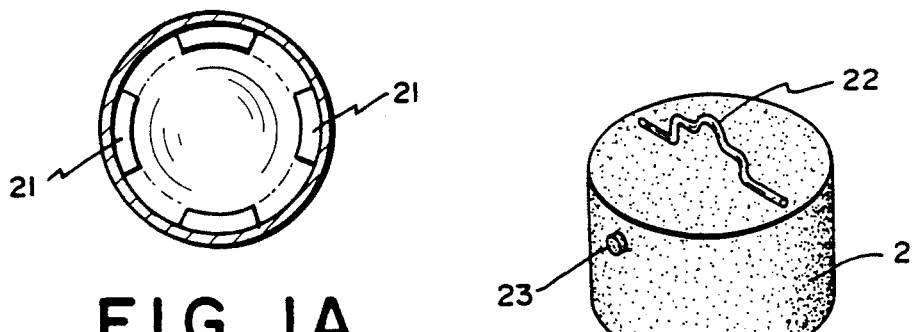
FIG. 1A is a bottom view of the cover of the spring pressure assembly according to the present invention.
Figure 1:
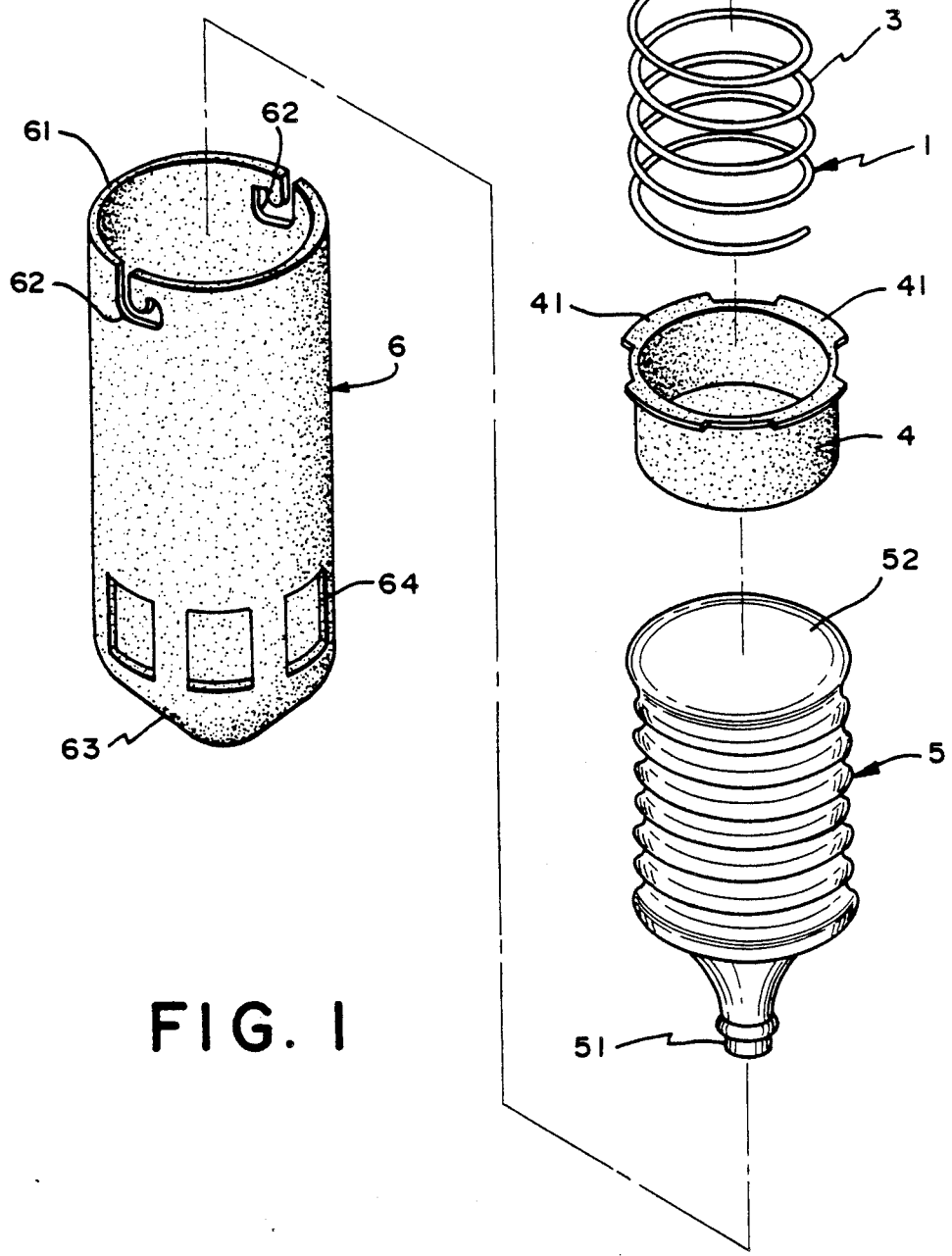
FIG. 1 is a perspective exploded view of the present invention.

With reference to FIG. 1, an automatic drip bottle set is shown as including a spring pressure assembly 1, an expansion drip bottle 5 and a hollow cylinder 6.

The spring pressure assembly 1 is comprised of a cover 2, a spring 3 and a basin 4. The cover 2 is provided with several stop plates 21 integrally formed on its inner bottom, as shown in FIG. 1A, to engage with corresponding retainer plates 41 which are integrally formed on the top of the basin 4 and arranged to project outwardly therefrom, for stable positioning when the cover 2 and the basin 4 are connected. The spring 3 is received in the basin 4. When the basin 4 and the cover 2 are firmly retained, the spring 3 will provide a pressure force to urge the basin 4 downwardly. Further, the cover 2 of spring pressure assembly 1 includes two opposed dowels 23 integrally formed on the outer surface at opposite positions located 180° from each other, to respectively engage with the two opposed "J" shaped notches 62 of cylinder 6 for connecting cover 2 with the cylinder 6. The "J" shaped notches 62 are provided on the top end of the cylinder 6. The cover 2 is also provided with a stepped hanger 22 mounted thereon at the top for suspending the assembled drip bottle set. The hollow cylinder 6 includes a conical bottom 63 and a plurality of peripheral inspection windows 64 through which the amount of the infusion solution contained within cylinder 6 may be viewed. Cylinder 6 includes a through-hole 65 at its bottom end through which the head 51 of the expansion drip bottle 5 is inserted to protrude therebeyond.

Figure 2:
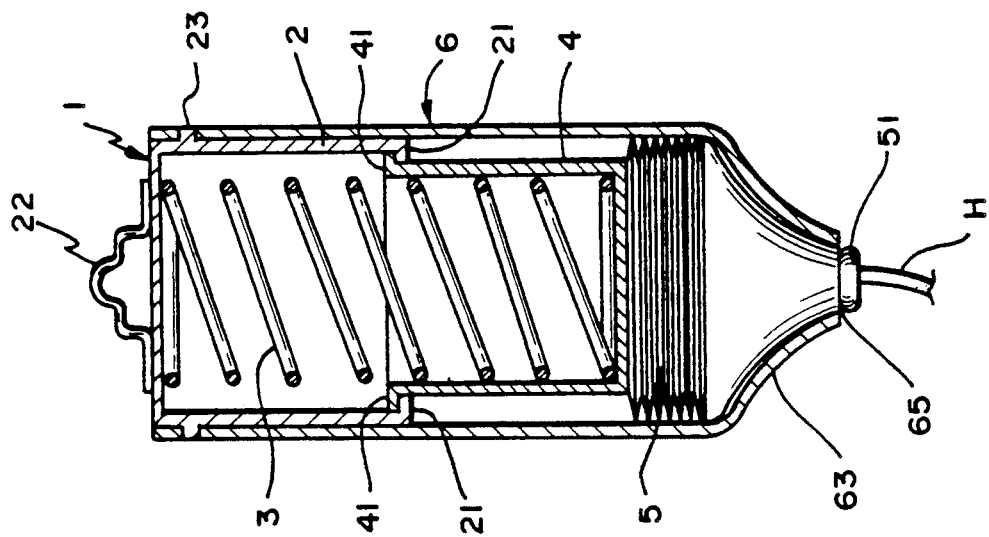
FIG. 2 is a sectional view of the present invention in assembled form and when it is fully filled with infusion solution.
Figure 3:
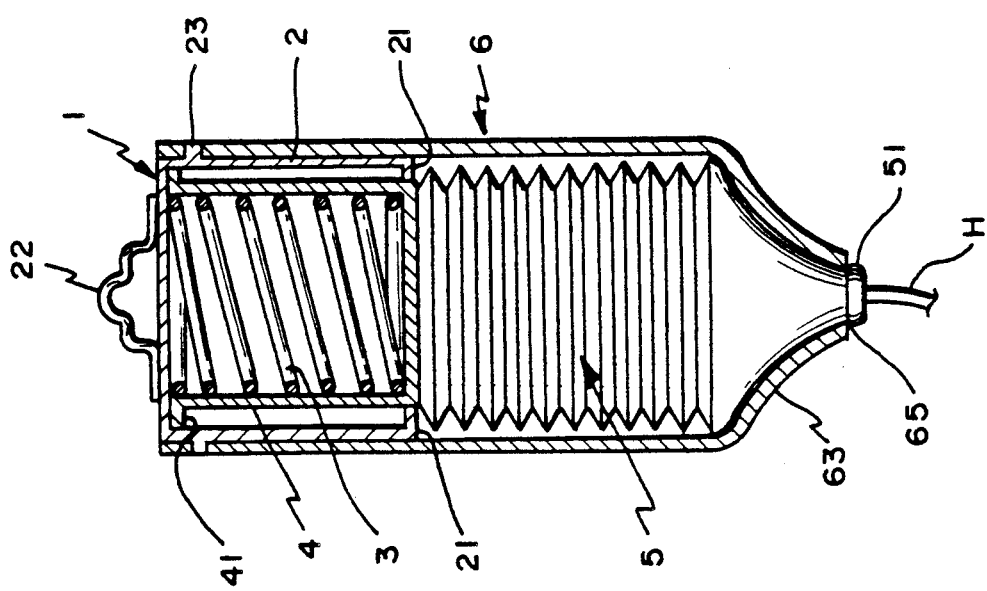
FIG. 3 is a sectional view of the present invention shown in FIG. 2 after infusion solution has been completely infused.

When assembled, as shown in FIGS. 2 and 3, the infusion solution contained expansion drip bottle 5 is inverted and disposed in the hollow cylinder 6 from the top end 61 with the head 51 inserted through the through-hole 65 to firmly position bottle 5 within cylinder 6. The spring pressure assembly 1 is disposed in the hollow cylinder 6 with the dowels 23 respectively turned in the "J" shaped notches 62 to secure assembly 1 to cylinder 6. This permits spring pressure assembly 1 to press against the top surface 52 of the expansion drip bottle 5. When the drip infusion process is started and the infusion solution be infused through the infusion tubing H to drip into the patient's body, the basin 4 is urged by the spring 3 to apply uniform pressure on the expansion drip bottle 5. This causes the expansion drip bottle 5 to be gradually contracted to smoothly compress the infusion solution through the infusion tubing H into the patient's body.

I claim:
1. An automatic drip bottle set comprising:
(a) a hollow cylinder including a conical-shaped bottom portion terminating in an axially disposed through-hole and a top portion provided with a pair of opposed J-shaped notches;
(b) a compressible drip bottle for containing infusion solution and being receivable within the hollow cylinder, the drip bottle including a head portion for insertion through the through-hole of the hollow cylinder when the drip bottle is received therein; and
(c) a spring pressure assembly including a basin, a cover and a spring, the basin including a plurality of retainer plates extending outwardly from a top portion thereof, the cover including a stepped hanger at a top portion thereof, a pair of opposed dowels extending outwardly from an outer surface of the cover for corresponding engagement within the pair of opposed of J-shaped notches for connecting the spring pressure assembly to the hollow cylinder, and a plurality of stop plates extending inwardly from a bottom portion of the cover for matching engagement with the retainer plates to slidably secure the basin within the cover, and the spring being disposed within the basin and cover for urging the basin downwardly against the drip bottle and providing a uniform pressing force against the drip bottle to compress same and cause the infusion solution contained therein to be smoothly infused into the body of a patient.

2. The automatic drip bottle set of claim 1 wherein the hollow cylinder further includes a plurality of windows spaced around its periphery to permit visual inspection of the infusion solution contained within the drip bottle.

* * * * *